US009545519B2

United States Patent
Aslam et al.

(10) Patent No.: US 9,545,519 B2
(45) Date of Patent: Jan. 17, 2017

(54) ACTIVE INTERFACE DEVICE

(75) Inventors: Junaid Aslam, Gujrat (PK); Patrick Merken, Montenaken (BE); Chris Van Hoof, Leuven (BE)

(73) Assignees: IMEC, Leuven (BE); Katholieke Universiteit Leuven, KU LEUVEN R&D, Leuven (BE)

( * ) Notice: Subject to any disclaimer, the term of this patent is extended or adjusted under 35 U.S.C. 154(b) by 774 days.

(21) Appl. No.: 12/840,002

(22) Filed: Jul. 20, 2010

(65) Prior Publication Data

US 2011/0015866 A1 Jan. 20, 2011

Related U.S. Application Data

(60) Provisional application No. 61/227,001, filed on Jul. 20, 2009.

(51) Int. Cl.
| | |
|---|---|
| *A61N 1/372* | (2006.01) |
| *G06Q 50/22* | (2012.01) |
| *G01N 33/487* | (2006.01) |
| *A61B 5/04* | (2006.01) |
| *A61N 1/02* | (2006.01) |

(52) U.S. Cl.
CPC ....... *A61N 1/37211* (2013.01); *A61B 5/04001* (2013.01); *A61B 5/04004* (2013.01); *A61N 1/025* (2013.01); *A61B 2562/0209* (2013.01); *A61B 2562/046* (2013.01)

(58) Field of Classification Search
CPC .... G06Q 50/22; G06Q 10/08; G01N 33/4836; G01N 33/48728; G01N 2035/00158
USPC .......................................................... 702/19
See application file for complete search history.

(56) References Cited

U.S. PATENT DOCUMENTS

| | | | | |
|---|---|---|---|---|
| 4,736,751 | A | * | 4/1988 | Gevins et al. ................ 600/545 |
| 7,335,972 | B2 | * | 2/2008 | Chanchani .......... B81C 1/00238 |
| | | | | 257/668 |
| 2002/0192637 | A1 | | 12/2002 | Parsons et al. |
| 2004/0106101 | A1 | * | 6/2004 | Evans .............................. 435/5 |
| 2005/0107893 | A1 | * | 5/2005 | Eversmann et al. ............ 700/48 |

(Continued)

FOREIGN PATENT DOCUMENTS

WO  WO2007058950  5/2007

OTHER PUBLICATIONS

European Search Report, European Patent Application 10152166 dated Jun. 3, 2010.

(Continued)

*Primary Examiner* — Gregory J Toatley
*Assistant Examiner* — Terence Stifter, Jr.
(74) *Attorney, Agent, or Firm* — McDonnell Boehnen Hulbert & Berghoff LLP

(57) ABSTRACT

An active interface device including a transducer or sensor array having a plurality of transducers or sensors arranged to transform a cell activity into an electrical signal, at least one detection unit for detecting the electrical signal(s), at least one recording unit for recording the electrical signal(s), comprising a plurality of recording channels arranged for being routed to the transducers or sensors, and at least one control unit. The control unit is arranged for addressing the transducers or sensors to the detection unit(s), for activating transducers or sensors, and for routing the recording channels to activated transducers or sensors.

21 Claims, 12 Drawing Sheets

(56) References Cited

U.S. PATENT DOCUMENTS

| | | |
|---|---|---|
| 2005/0203366 A1* | 9/2005 | Donoghue et al. ........... 600/378 |
| 2006/0089112 A1 | 4/2006 | Irazoqui-Pastor et al. |
| 2007/0129770 A1 | 6/2007 | Younis |
| 2009/0004685 A1* | 1/2009 | Huys et al. ..................... 435/29 |
| 2010/0145179 A1* | 6/2010 | Lin et al. ...................... 600/393 |

OTHER PUBLICATIONS

Frey, Urs et al., "An 11k-Electrode 126-Channel High-Density Microelectrode Array to Interact with Electrogenic Cells", in ISSCC 2007, San Francisco, California, Feb. 2007, pp. 158-159, 593.

Eversmann, Bjorn et al., "A 128×128 CMOS Biosensor Array for Extracellular Recording of Neural Activity", IEEE Journal of Solid-State Circuits, vol. 38, No. 12, Dec. 2003, pp. 2306-2317.

\* cited by examiner

ACTIVE INTERFACE DEVICE

CROSS-REFERENCE TO RELATED APPLICATIONS

The present application claims priority to U.S. Provisional Application No. 61/227,001 filed in the United States Patent and Trademark Office on Jul. 20, 2009, the entire contents of which is incorporated herein by reference.

FIELD

The present disclosure relates to the field of front-end interface devices comprising a plurality of transducers or sensors to be used as active neural sensors. In particular, the present disclosure relates to a device comprising an array of transducers or sensors as well as to a method for operating the interface devices.

Finally, the present disclosure also relates to the use of such interface devices in the in vitro or the in vivo fields.

BACKGROUND

There are two main methods for recording cell activity using large cellular (neural) interfaces comprising at least 128×128 sensors.

A first approach is based on a scanning method of the entire array of sensors.

One example of this method is disclosed in Eversmann et al., "A 128×128 CMOS Biosensor Array for Extracellular Recording of Neural Activity," IEEE Journal of Solid State Circuits, Vol. 38, No. 12, December 2003. In this document, the authors describe a method and a device in which there are 128 rows and 128 columns. The entire array of sensors is individually scanned at a sufficient scanning frequency (2 kiloframes per second, (kfps)). The scanning is done with a row and column addressing technique. Each row has one amplifier leading to a total of 128 amplifiers. These are further multiplexed 8 to 1 and thus there are 16 outputs. This information is sent off the chip to a PC where 16 A/D converters are used and the information is processed.

The amount of information to be processed is quite large, 32 MS/s (MegaSamples/second). This raises important problems for post processing of the information. As arrays get larger the amount of data to be processed also increases. An array of 256×256 sensors would require 131 MS/s. Furthermore, noise is also a concern as a recording amplifier has to be present in every sensor, the size of which has to be limited to keep the pitch of the sensor within a reasonable value; comparable to the size of a neuron (between about 20 μm and about 100 μm).

The second method is based on the assumption that not all sensors are in contact with a cell (neuron) and are therefore not of interest.

An example of this method is disclosed in U. Frey et al., "An 11k-electrode 126-channel High Density Microelectrode Array To Interact With Electrogenic Cells," in ISSCC 2007, San Francisco, Calif., February 2007, pp. 158-159, wherein, the authors describe a very large array with 11,000 sensors having 126 channels that are permanently routed to sensors of interest. The amount of data is consequently reduced and noise performance is improved as the sensors only require a routing circuitry.

Because of the scarcity of neurons on the sensors, the system is capable of recording most of the cellular activity. Nevertheless, all of the neurons are not observable, and the device is always limited to the number of channels available for routing. In this case, only 1.14% of the array is observable at any one time. Increasing the number of sensors will require an increase in the number of channels. Assuming a linear increase, for a 256×256 array, 504 channels will be required for the same system monitoring capability.

An overview of the methods used according to the state of the art is represented in FIG. 1.

SUMMARY

The present disclosure relates to an active interface device for detection and recording of cell activity, in particular in neural systems, comprising:
  a transducer or sensor array comprising a plurality of transducers or sensors arranged to transform a cell activity into an electrical signal;
  at least one detection unit for detecting the electrical signal(s);
  at least one recording unit for recording the electrical signal(s), comprising a plurality of recording channels arranged for being routed to the transducers or sensors;
  at least one control unit;
  wherein the control unit is arranged for addressing the transducers or sensors to the detection unit(s), for activating transducers or sensors, and for routing the recording channels to activated transducers or sensors. In particular, the control unit decides upon detection of electrical signal(s) to route recording channels to activated transducers or sensors.

The transducer or sensor can be considered as a pixel in a network (array).

Advantageously, the device, according to the present disclosure, comprises at least two amplifying blocks or units for amplifying the electrical signal(s), wherein the first amplification is performed by first amplifying means being present in the detection unit, and the second amplification is performed by second amplifying means being present in the recording unit.

Preferably, the device, according to the present disclosure, has a ratio of the gain between the first amplifying means and the second amplifying means of at least of 5 and preferably superior to 10.

Preferably, the first amplifying means are faster than the second amplifying means.

Preferably, the first amplifying means generate more noise than the second amplifying means.

In particular, the first amplifying means is defined by a high gain, for a noise being comprised between 20 μVrms-100 μVrms and a bandwidth between 1 MHz-3 MHz.

In particular, the second amplifying means is defined by a low gain, for a noise being comprised between 3 μVrms-15 μVrms and a bandwidth between 5 KHz-10 KHz.

Preferably, the detection unit comprises a first amplifying means arranged for amplifying the electrical signal.

Preferably, the detection unit comprises at least one comparator arranged to compare the amplified electrical signal with a predetermined threshold signal. Activity is detected if the amplified electrical signal is above the predetermined threshold signal.

Preferably, each transducer or sensor comprises at least one buffer.

Preferably, the detection unit comprises at least one sample and hold capacitor.

Preferably, the recording unit comprises a second amplifying means, the second amplifying means arranged for amplifying the (detected) electrical signal.

Preferably, the first and/or second amplifying means comprise at least one amplification stage.

Preferably, the at least one amplification stage comprises at least one low noise amplifier.

Preferably, the device according to the present disclosure further comprises at least one stimulation unit arranged for sending electrical stimulation signals to at least one transducer of the transducer or sensor array.

Preferably, the device according to the present disclosure further comprises a post-processing unit.

Preferably, the control unit comprises an on-chip controller.

Preferably, the control unit comprises a Field-Programmable Gate Array.

Preferably, the transducer or sensor array is divided into transducer or sensor subarrays.

Preferably, each transducer or sensor subarray comprises at least one detector unit.

Preferably, each transducer or sensor subarray comprises at least one recording unit.

Preferably, each transducer or sensor subarray comprises at least one control unit.

Preferably, each transducer or sensor subarray comprises at least one stimulation unit.

Preferably, each transducer or sensor subarray comprises at least one post-processing unit.

The present disclosure also relates to a method for recording cell activity with a transducer or sensor array comprising a plurality of transducers or sensors, wherein, for each transducer or sensor, the following steps are performed:
- a) addressing a transducer of the transducer or sensor array or addressing a transducer of a predetermined subset of transducers or sensors of the transducer or sensor array;
- b) activating the transducer or sensor;
- c) receiving from the activated transducer or sensor any electrical signal (possibly resulting from cell activity);
- d) amplifying the electrical signal by a first amplifying means;
- e) comparing the electrical signal to a predetermined threshold signal;
- f) determining by using the comparison result of step e) that the electrical signal corresponds to a cell activity;
- g) for any electrical signal corresponding to a cell activity routing a recording channel to the activated transducer or sensor;
- h) recording the electrical signal from the activated transducer or sensor.

Preferably, in the method according to the present disclosure, the amplifying step d) is performed with a first amplifying means having a high gain, in the detection stage defined here above as steps a) to f), and dependent on the outcome of the comparison, this is followed by a second amplification at a low gain performed during the recording stage defined here above as steps g) to h).

Preferably, in the method according to the present disclosure, the ratio of the gain between the first amplifying stage and the second amplifying stage is at least 5 and preferably superior to 10.

Preferably, the sequence of steps a) to h) for the next or subsequent transducer or sensor starts between steps c) and d).

Preferably, the step a) to h) are repeated for the next or subsequent transducer or sensor.

Preferably, the method according to the present disclosure further comprises—after step h)—the step of sequentially sending the recorded electrical signals (recorded cell activity) to a post-processing unit.

Preferably, the step of comparing is performed by a detection unit.

Preferably, the step of determining—if the acquired electrical signal corresponds to cell activity—is performed by a control unit.

Preferably, the step of routing is performed by the control unit.

Preferably, the step of recording is performed by a recording unit.

BRIEF DESCRIPTION OF THE DRAWINGS

FIG. 3($b$) represents a embodiment of the components of the transducer/sensor array and corresponding to the schema block of FIG. 2.

FIG. 9($b$) represents an example of the output from a crude amplifier comprised in the detection unit according to the present disclosure.

DETAILED DESCRIPTION

Figure 1:
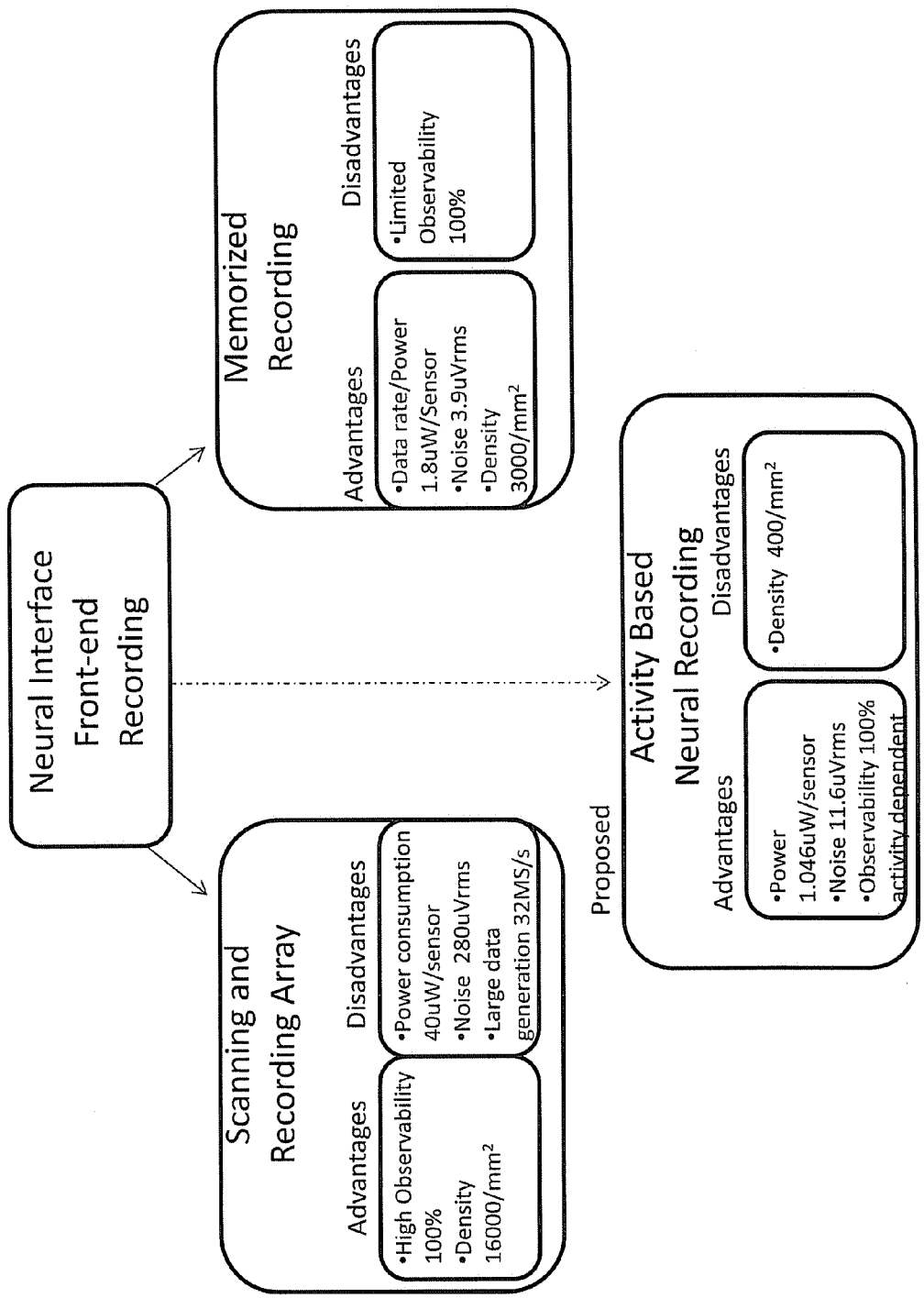
FIG. 1 represents a comparison of the state of the art with the new proposed interface device for neural front-end recording system.

According to a first aspect, the present disclosure is related to a sensor array having a plurality of sensors arranged for stimulating neurons and recording neural activity. The network comprises a first amplifying block or unit and a second amplifying block or unit and (with) a digital control block (unit). The first amplifying block is arranged for detecting neural activity. The control block (unit) is arranged for addressing the sensors, for routing the channels to these sensors and for activating the second amplifying block. The second amplifying block is arranged for recording the neural activity.

An intelligent real-time routing system is provided that allocates available resources or channels based on neural activity. The network of the present disclosure can comprise a sensor array which is scanned with a first amplifying means (also called block) or crude circuitry which is optimized for area (surface) and very high gain and high speed for the detection of neural activity.

Once activity at a sensor or pixel or a set of sensors or pixels is detected, an available channel within the array is routed by the control block (unit) to the corresponding sensor pixel for recording the signal. In the meantime, the detection unit proceeds with scanning the sensor array.

The control block (unit) can designate a set of sensors as one block in case a neuron is present on more than one sensor or its signal is being received at neighboring sensors.

Recording can be performed via one of the free recording channels within the array by the second amplifying block or (also called) the fine amplifier.

The recording channel can comprise of fine amplifiers divided into stages which are present within the array.

Further, the recording channel can comprise any post processing, like A/D converters or "spike" filtering, which is preferably present outside the array.

The fine amplifiers are preferably optimized for low power, low noise, and area.

The recording from the recording channel can tell if the detection of neural activity (spike) by the neural activity detection system is true or false. The probability of a false detection and hence a wrong routing of a channel depends on the amplitude of the signal versus the noise in the neural activity detection unit.

The recording channels are accorded resources to record neural activity. These resources are preferably allocated based on need in real time. By intelligently using the limited channels, activity can be recorded from the entire sensor array, because there is no need to permanently route any channel to a given sensor. At the same time, the generation of large amounts of data and the power consumption can be minimized because the recording channels are not used needlessly all the time when there is no activity.

Furthermore, the sensor network is an active, front-end interface device arranged for scanning and recording a transducer and/or sensor array and arranged for sending the recorded data (being the useful data) to a post-processing block. Recording is only performed when neuron activity is detected. Only a limited amount of data needs to be forwarded to a post-processing block.

In a preferred embodiment, the sensor network is arranged in a 3D integrated system. A plurality of sensor networks can be implemented on several top dies. The bottom die has a number of recording channels. The number of channels is preferably based on the available area in the bottom die. The sensors on the top die can be routed to any of the recording channels on the bottom die through the 3D vias. This way, given that the area is fixed, a larger number of channels are available for each layer or sub-array than would be if only a single die would be used.

These same channels can also be used for stimulation, if a stimulation circuitry is placed on the bottom die. Both dies can be made in separate technologies to optimize the readout and reduce costs.

The present invention will be described with respect to particular embodiments and with reference to specific drawings but the invention is not limited thereto but only by the claims.

The drawings described are only schematic and are non-limiting.

In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting of only components A and B. It means that with respect to the present invention, the only relevant components of the device are A and B.

Figure 2:
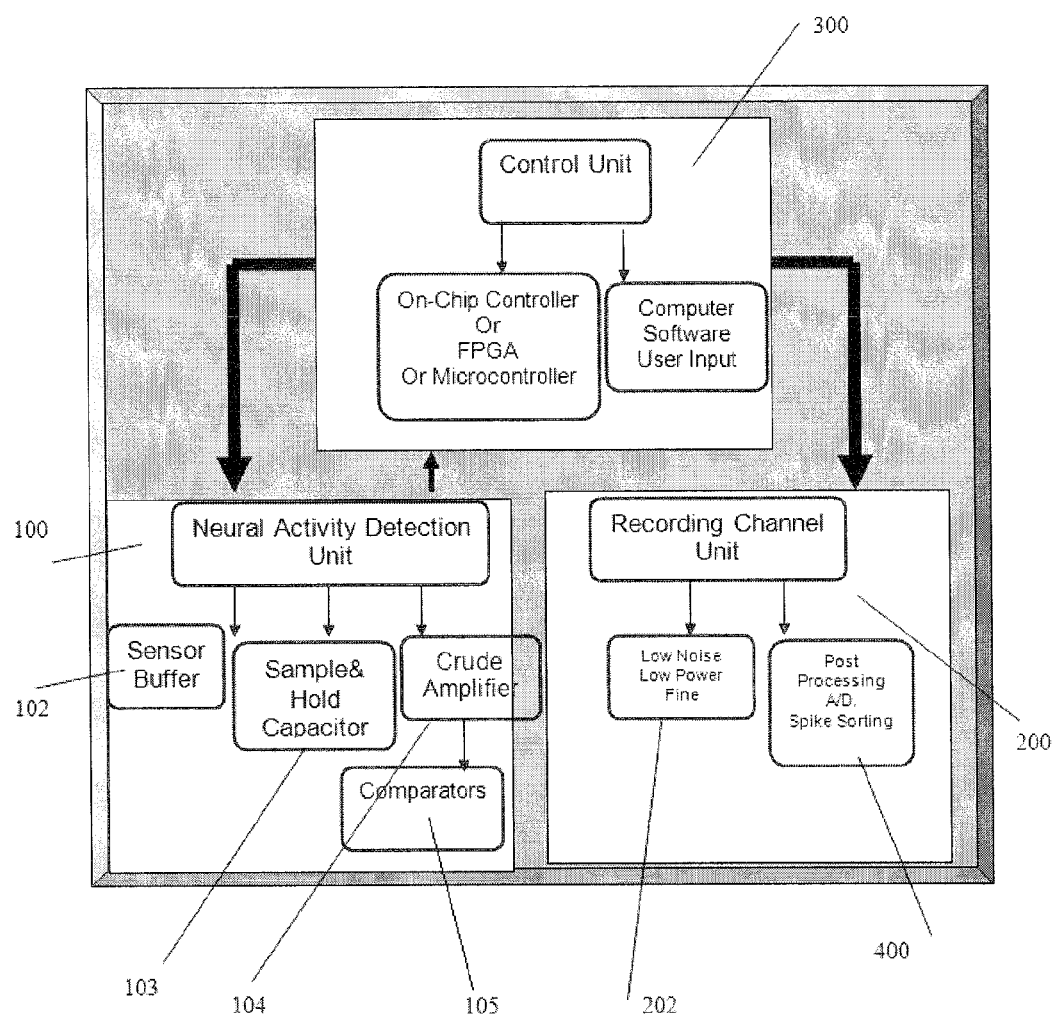
FIG. 2 represents a block diagram of several components of an interface device according to the present disclosure.

An interface device according to the present disclosure is displayed as a schema block in FIG. 2.

Figure 3A:
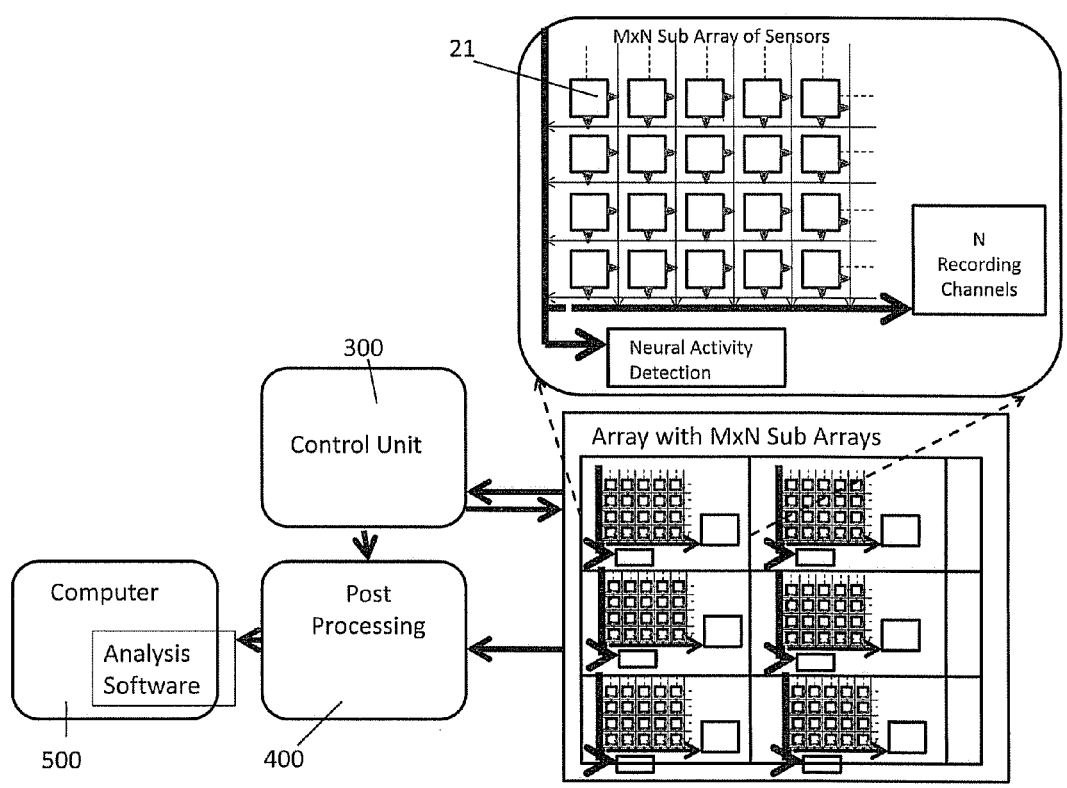
FIG. 3($a$) represents a specific embodiment of such an interface device as generally described in FIG. 2 wherein the array of transducer/sensor is in the form of M×N subarrays.
Figure 3B:
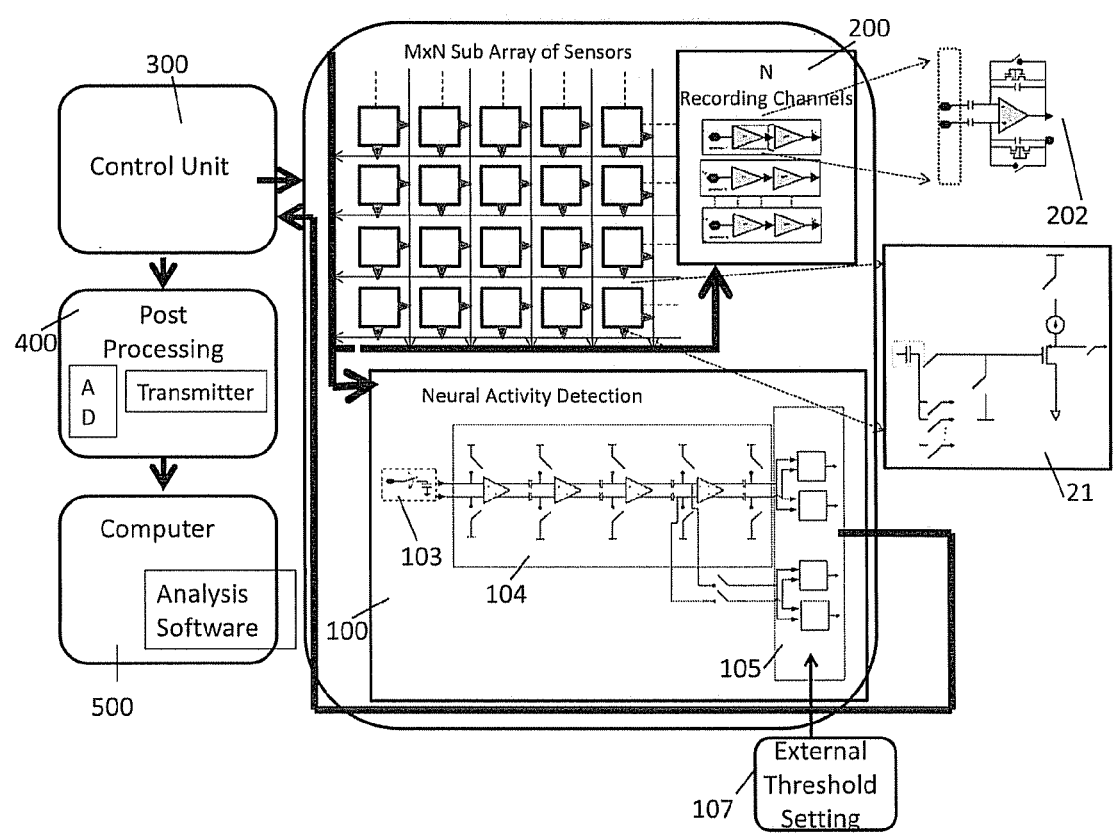

FIGS. 3(a) and 3(b) represent an implementation of a specific embodiment for M×N sub array of transducers with neural activity detection for N recording channels.

Figure 4:
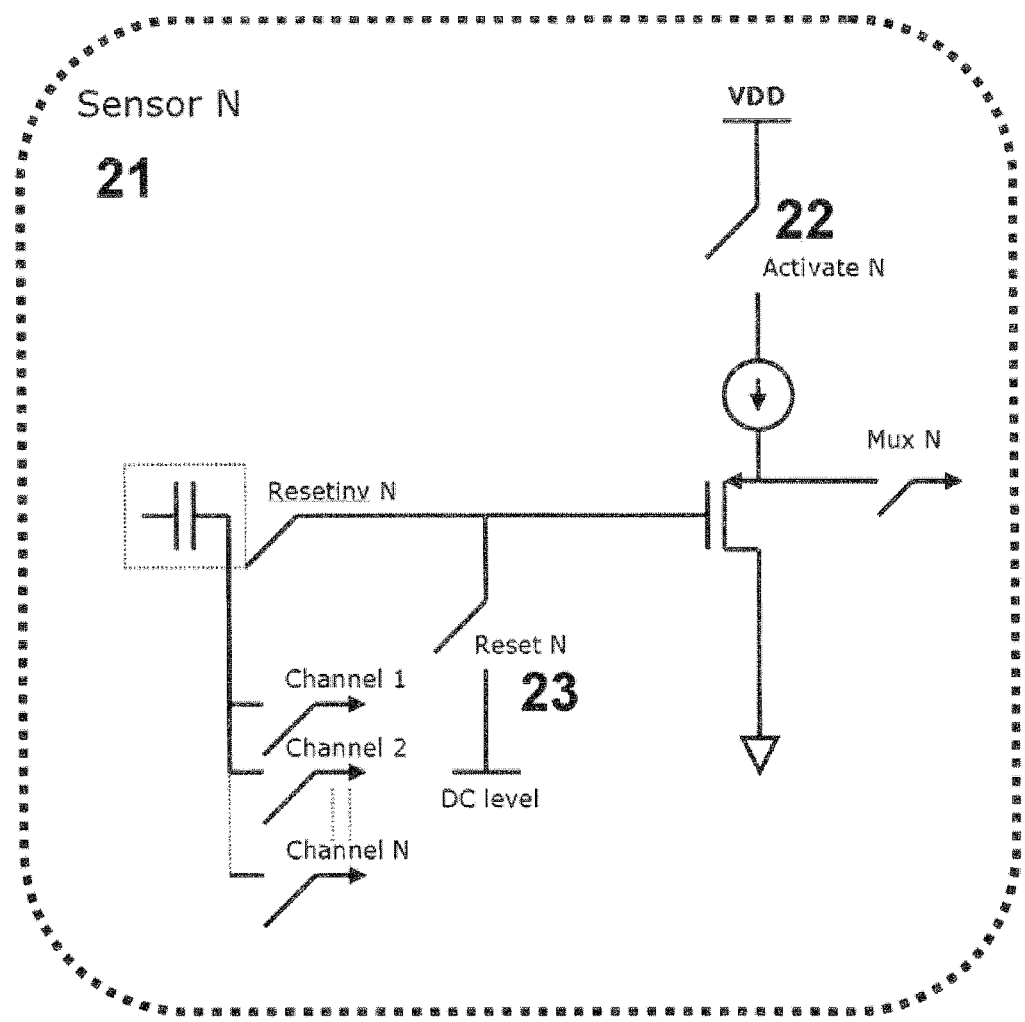
FIG. 4 represents an example of a transducer/sensor.
Figure 5:
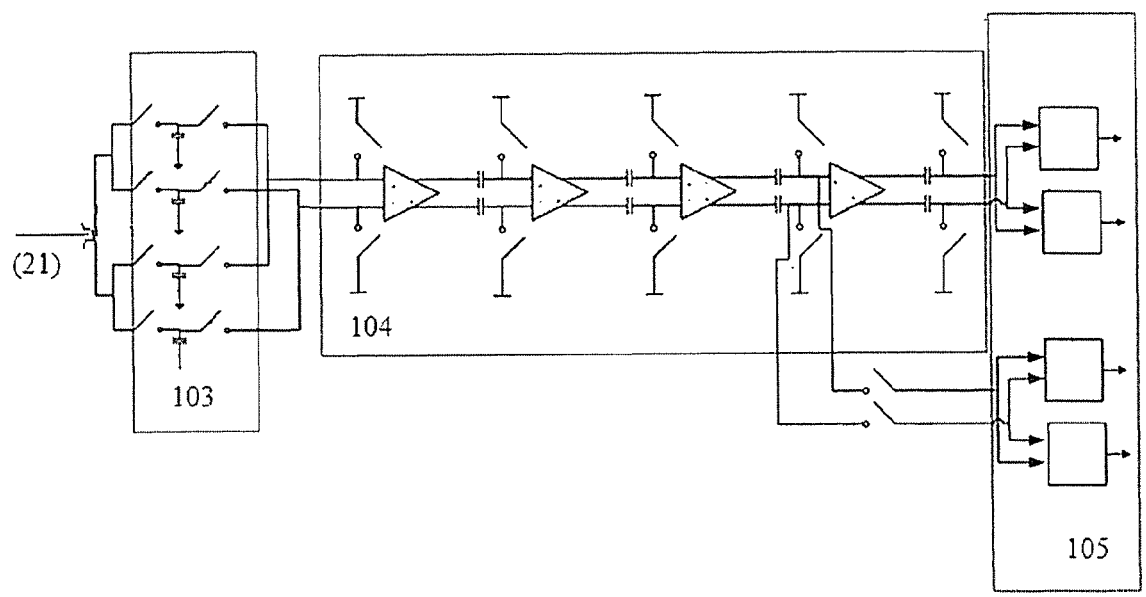
FIG. 5 represents an example of a detection unit used in the present disclosure.
Figure 6:
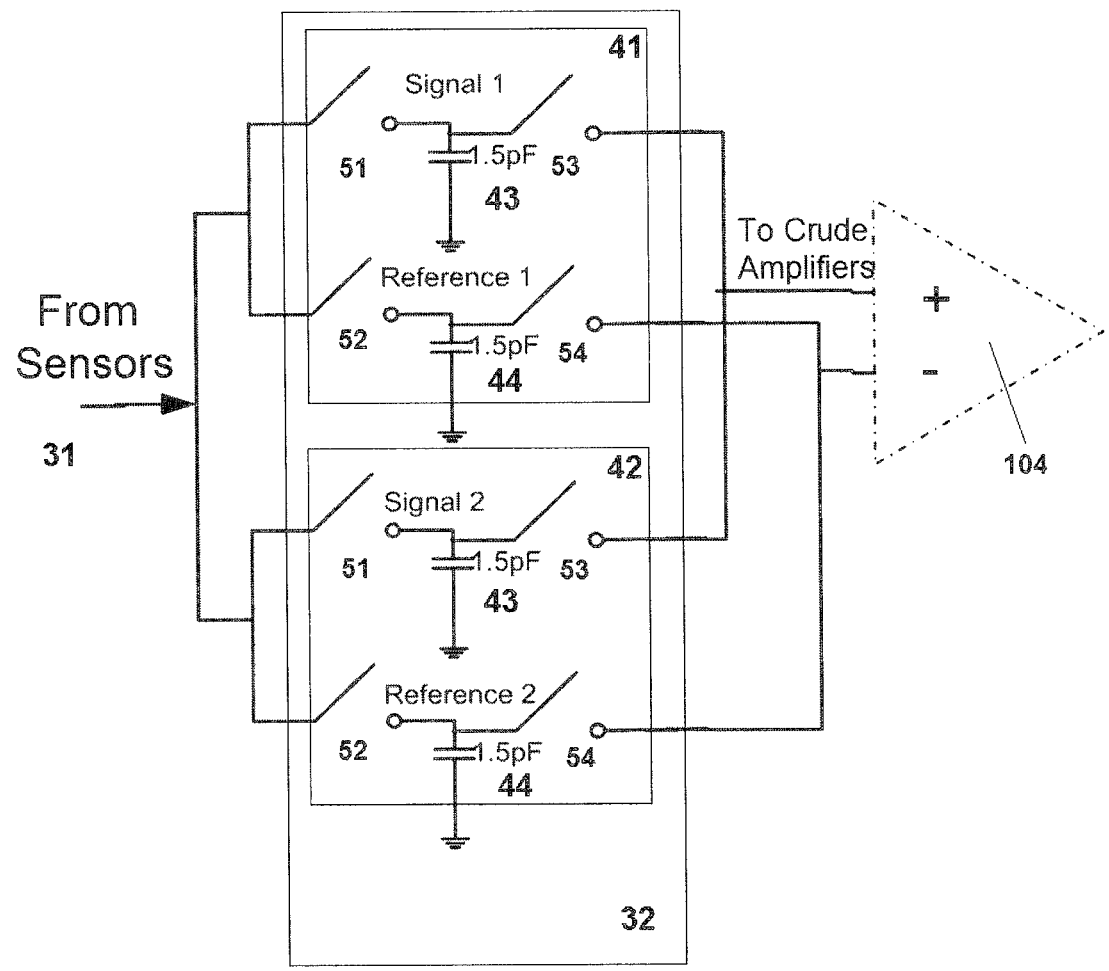
FIG. 6 represents an example of sample and hold capacitors of the detection unit.

FIGS. 4, 5, and 6 represent in detail particular embodiments of constituting elements of the devices as represented in FIGS. 2, 3(a), and 3(b). In particular, FIG. 4 displays an example of a transducer or sensor used for neural detection.

The device according to the present disclosure, in particular as described in FIGS. 2, 3(a), and 3(b), comprises a transducer array comprising a plurality of transducers, at least one detection unit 100 arranged for detecting cell activity, at least one recording unit 200 arranged for recording cell activity, and comprising a plurality of recording channels, and at least one control unit 300 for controlling the detection unit(s), the recording channel(s) and the recording unit(s).

In the present disclosure, the term "transducer" refers to any device arranged for transforming cell activity into an electrical signal.

In the present disclosure, the term "cell activity" refers to any signal produced by the cell, irrespective of the nature of the signal. The signal can be a mechanical stress, a release of ions, a release of neurotransmitters, an electrical signal, etc.

Preferably, the detection unit 100 comprises amplifying means 104 arranged for amplifying electrical signals resulting from cell activity.

According to a preferred embodiment as represented in FIG. 2 and in particular in FIG. 5, the detection unit 100 comprises at least the following elements sample and hold capacitor(s) 103, crude amplifier(s) 104, and comparator(s) 105.

The threshold voltage defines at which input voltage, the comparator will give the logical value 1. If the threshold voltage is set below the noise at the output of the "crude" amplifier means, the comparator will be triggered with this noise. So, the threshold voltage is at a level above this noise at the output of the "crude" amplifier means. Usually noise is defined as input referred, meaning that the noise would be at the input of the "crude" amplifier means rather than the output. But to make it more simple lets just say that the noise is present at the output of the "crude" amplifier means.

Accordingly, the detection unit 100 comprises a first amplifying means (or stage) 104 also called hereunder "crude" amplifying means (stage).

Preferably, the recording channel unit 200 comprises a second amplifying means (or stage) 202 also called hereunder "fine" amplifying means (stage).

The detection unit 100 is arranged for comparing the electrical signal coming from a transducer 21 to a reference signal—called reference threshold signal 107—and is further arranged to send the comparison result to the control unit 300.

An example of transducer or sensor 21 is displayed at FIG. 4.

For example, the transducers are sensors 21 suitable for electrophysiological measurements such as planar electrodes on an insulating glass substrate.

For example, the sensors can be electrochemical sensors based on enzymatic catalysis of a reaction that produces or consumes electrons, namely redox enzymes.

Another example of suitable sensors are CMOS based sensors.

Another example of suitable sensors are piezoelectric sensors.

Preferably, each transducer of the transducer or sensor 21 array comprises at least one buffer (represented as 102 in FIG. 2).

In the present disclosure, the term "buffer" can refer to a device that provides impedance transformation from one circuit to another.

Preferably, the buffer(s) is (are) implemented as gated source followers.

Preferably, each transducer or sensor 21 is activated sequentially by the control unit 300.

Preferably, the transducer or sensor 21 can be either in an active state or in an inactive state.

The term "active state" refers to a state wherein the transducer or sensor 21 is able to transform cell activity into an electrical signal.

The term "inactive state" refers to a state wherein the transducer or sensor 21 is not able to transform cell activity into an electrical signal.

The state of the transducer or sensor is controlled by the control unit 300.

The transient activation of a transducer or sensor reduces power consumption and avoids heating the cells which are on top of the transducer or sensor.

The transducer or sensor 21 as displayed at FIG. 4 can be addressed using a set of addressing switches 22.

The transducer or sensor 21 as displayed at FIG. 4 can be activated by turning on the switch 22. The switch 22 has two states: ON and OFF.

Preferably, the electrical signal is amplified (in 104) prior to the comparison (in 105) with the reference threshold signal through e.g. an external threshold setting 107 as represented in FIG. 3(*b*).

The result of the comparison is sent to one of the at least one control unit 300.

The detection threshold 107 for the comparators can be set externally by setting the reference voltage of the comparator to a predetermined level above the noise.

For example, if the noise is given by $\sigma$, then an acceptable interval of input noise can be 20 $\mu$Vrms$\leq\sigma\leq$100 $\mu$Vrms for a possible reference voltage of $1\sigma\sim5\sigma$ (input noise multiplied by the gain of the crude amplifier).

If this noise is $\sigma$. Then the acceptable interval of threshold is $1\sigma$ to $5\sigma$, meaning 1 times $\sigma$ or 5 times $\sigma$.

If the input referred noise is 100 $\mu$Vrms then output referred noise $\sigma$ can be calculated as 100 $\mu$Vrms$\cdot$G where G is the Gain of the "crude" amplifier means.

Figure 7:
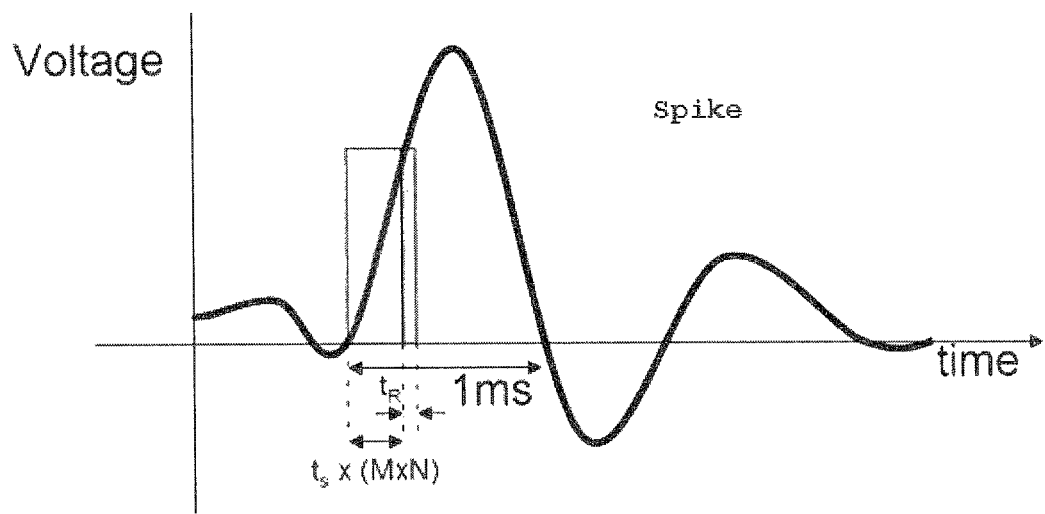
FIG. 7 represents an example of the scanning pulse of a cell activity (neural spike) which is a representation of the voltage versus line.

The intervals for the input referred noise are comprised between 20 $\mu$Vrms to 100 $\mu$Vrms for a "spike" (cell activity) between 100 $\mu$V to 5 mV. Typically, as represented in FIG. 7, a spike has a duration of 1 ms.

Typically, the noise for "crude" amplifier means is comprised between 20 $\mu$Vrms-100 $\mu$Vrms while the noise for the "fine" amplifier means is comprised between 3 $\mu$Vrms-15 $\mu$Vrms.

Preferably, for a bandwidth comprised between 1 MHz-3 MHz for the "crude" amplifier means and between 5-10 KHz for the "fine" amplifier means.

The power of the "crude" amplifier means is comprised between 100 $\mu$V and 200 $\mu$V while the power for the "fine" amplifier means is comprised between 5 $\mu$V and 15 $\mu$V.

The "crude" amplifier means 104 with conjunction with the comparator 105 gives a signal if there is cell activity (presence of a spike as in FIG. 7). Sometimes the comparator 105 will be triggered by noise in the "crude" amplifier means 104 itself. The "crude" amplifier means 104 can also be non-linear.

The "fine" amplifier means is connected when there is cell activity. It is the noise, and the output of the "fine" amplifier means, which will decide if the activity detected with the help of the "crude" amplifier means 104, the comparators 105, and the buffers 102 in the sensors, is an actual "spike" or is due only to detected noise.

Figure 8:
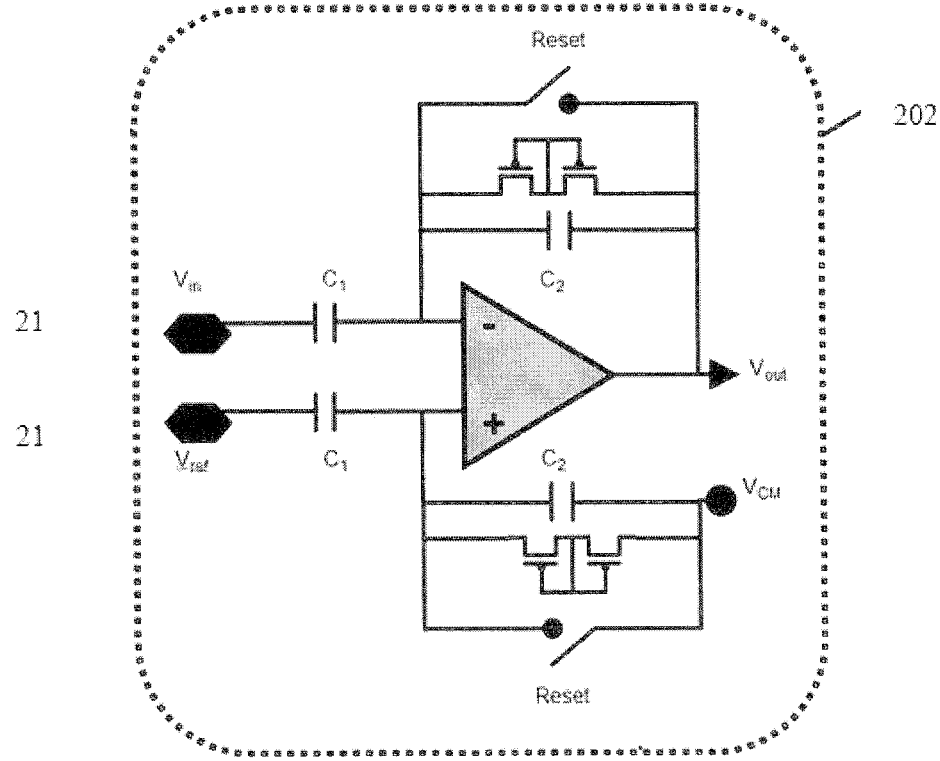
FIG. 8 represents an example of a low noise and low consumption fine amplifier.

An example of "fine" amplifier means is given in FIG. 8.

Preferably, the detection unit 100 comprises (sensors) buffers 102 for driving the sample and hold capacitors 103 as represented in FIG. 5.

Preferably, the detection unit 100 comprises sample and hold capacitor(s) 103 for the implementating of Correlated Double Sampling (CDS) for removing the offset in the buffers of the transducers and to remove 1/f noise in these buffers.

Preferably, the buffers 102 are arranged for driving the sample and hold capacitors 103.

Preferably, the buffers 102 are implemented as source followers.

An example of sample and hold capacitors 103 is shown in FIG. 6.

In this example, a detection unit 100 comprises two pairs of sample and hold capacitors (41, 42) comprising upstream switches (51, 52) and downstream switches (53, 54). These switches are controlled by the control unit 300.

Each pair of sample and hold capacitors has a signal capacitor 43 and a reset capacitor 44 which are arranged to remove the offset in the source followers.

As shown in FIG. 6, the signal capacitor 43 samples and holds the signal plus the offset present in the source follower while the reference capacitor 44 holds just the offset by resetting the source follower by activating the reset switch 23 as shown in FIG. 4. This helps to remove the offset.

The presence of two pairs of sample and hold capacitors (41, 42) reduces power consumption. Indeed, one pair of capacitors samples the signal from the currently addressed $t_{i+1}$ transducer or sensor while the other pair holds the value of the previously addressed transducer $t_i$ or sensor for the "crude" amplifier(s) 104.

Preferably, the "crude" amplifier means 104 is designed for high bandwidth, high gain, and area and compromised on noise and gain error since the primary function of these is not to record the activity but just to detect it.

Preferably, the amplifiers 104 are designed for low area (surface) such that the average pitch of the transducers or sensors 21, including the distance between the "crude" amplifier means 104 and the recording channels 200, does not exceed 50 μm.

The detection of an electrical signal resulting from cell activity requires very high gain to overcome the mismatch in the comparators.

In the present disclosure, the highest gain needed refers to the ratio between the value of the estimated mismatch in the comparator and the value of the smallest signal that has to be detected.

The offset in the amplifiers can be removed by output offset cancellation.

Alternatively, the offset can be removed by input offset cancellation.

The control unit 300 is arranged for addressing a transducer or a sensor 21 of the transducer array (M×N) to a detection unit 100.

The control unit 300 is arranged to activate a transducer or a sensor 21 subsequent to its addressing.

The control unit 300 can sequentially activate each transducer or a sensor 21 of the transducer array.

The control unit 300 can sequentially activate each transducer or a sensor 21 belonging to a predetermined subset of transducers.

In the present disclosure, the term "next" or "subsequent" preferably refers to the a temporal sequence.

Preferably, the control unit 300 is arranged to determine, based on the result of the comparison made by the detection unit, if a transducer or a sensor 21 has received from a transducer or a sensor 21 an electrical signal resulting from cell activity.

The control unit 300 is further arranged for routing (connecting) a recording channel to a transducer or sensor for which a cell activity has been detected according to the comparison.

Preferably, the control unit 300 is preferably further arranged for addressing the transducers or sensors, for activating the transducers or sensors 21, and for routing the recording channels 200.

The recorded signal of this recording channel will confirm if the signal detection by the detection unit 100 was caused by cell activity or by the noise in the detection unit 100.

The externally set reference 107 of the comparator 105 in the detection unit 100 will control how much the detection unit 100 is sensitive to noise in the detection unit 100.

Preferably, the control unit 300 comprises an on-chip controller, a FPGA, or any other microcontroller known to the person skilled in the art.

The probability of a false detection and therefore of wrong channel's routing depends on the ratio between the amplitude of the signal and the mean amplitude of the noise of the detection unit 100.

Preferably, the recording channel unit 200 comprises at least one recording channel (and preferably N channels).

Preferably, each recording channel unit 200 is arranged for recording the signal of one sensor at any given time.

Preferably, the recording channel unit 200 further comprises amplifying means 202, so called "fine amplifying" means.

Preferably, each recording channel of the recording channel unit 200 comprises at least one stage of amplification.

Preferably, each stage comprises at least one low noise and low power consumption fine amplifier.

Preferably, the amplifying means 104 of the detection unit 100 is faster than the amplifying means 203 of recording channel unit 200.

Preferably, the amplifying means 104 of the detection unit 100 generates more noise than the amplifying means 202 of the recording channel unit 200.

Preferably, the term "low noise fine amplifier" refers to an amplifier having a noise level between 2 $\mu V_{rms}$ and 15 $\mu V_{rms}$.

Preferably, the term "low power consumption fine amplifier" refers to an amplifier consuming between 3 μW and 35 μW.

The amplifier comprises two inputs. The first input $V_{in}$ is connected to the transducer or the sensor 21 from which an electrical signal is to be recorded, whereas the second input $V_{ref}$ is connected to a transducer or a sensor 21 defined as reference transducer or sensor 21. This allows differential recording and reduces the effect of external noise.

Examples of frequency response of the fine amplifier as well as example of noise measurements are shown in FIG. 9(*a*).

Examples of measurements of the detection unit are shown in FIG. 9(*b*).

FIG. 9(*b*) shows the output of the "crude" amplifier means after a square wave is given as an input to one of the transducer or the sensor 21 through a capacitively coupled input. The scanning is being done between four transducers or sensors 21.

Preferably, the transducer array or sensor 21 array comprises at least one stimulation unit.

Preferably the stimulation can be done on each transducer or sensor 21 individually.

Preferably, each stimulation unit uses the recording channels for sending stimulation signals to the transducers or sensors 21.

In the present disclosure, the term "stimulation signal" refers to any electrical signal generated by the stimulation unit leading to the generation of cell activity by a cell or a group of cells.

Preferably, the device according to the present disclosure also comprises a post-processing unit 400.

The post-processing unit 400 is arranged for processing the recorded data.

For example, the recorded data is converted into a digital signal by an Analog-to-Digital converter before being transmitted to an external device 500 e.g. computer for analyzing the recorded information.

Another aspect of the present disclosure relates to a method for detecting and recording cell activity by means of a transducer array or sensor 21 array comprising a plurality of transducers or sensors.

The present disclosure also relates to a method that routes recording channel(s) to transducer(s) or sensor(s) 21 for which a cell activity has been detected.

The recording channels are resources at the disposal of the transducer or sensor 21 array to record cell activity. These resources are allocated based on real-time needs. By intelligently using the limited number of channels, activity can be recorded from the entire transducer or sensor 21 array as there is no need to permanently route any channel to a given sensor. Moreover, there is no need to generate large amounts of data, and power consumption is saved, as there is no use of the recording channels needlessly all the time when there is no activity.

Preferably, the control unit is arranged for generating control signals for controlling the detection and the recording channels units (100 and 200).

Whereby the control signals for controlling the detection unit 100 comprise signals for turning on and addressing the sensor buffer 102 and resetting the sensor buffer. The control signals further comprise signals for controlling the connection of the currently addressed sensor buffer 102 to the sample and hold capacitor(s) 103 and the connection of the sample and hold capacitor(s) to the "crude" amplifier(s) 104 as well as the timing of these connections.

The control signals further comprise signals for controlling the removal of offset of the "crude" amplifier means 104.

Preferably, the control signals are arranged as clocks for the comparator 105 present after the "crude" amplifier means 104.

The control signals for controlling the recording unit comprise activation signals for turning on the recording channel 200 and resetting the amplification stages 104 and for connecting the recording unit 200 to the necessary sensors.

Preferably, the step of generating control signals for controlling the detection further comprises sending signals for turning on and addressing the sensor buffer 102. The step further comprises connecting the addressed sensor buffer 102 to the sample and hold capacitors 103 and connecting the sample and hold capacitors 103 to the amplifying means 104.

Preferably, the step of generating control signals for controlling the recording further comprises sending signals for turning on the recording channel 200 and resetting the amplification stages 202 and for connecting the recording unit to the necessary sensors.

Preferably, the step of activating each transducer or sensor 21 of a plurality (array) comprises activating each transducer or sensor 21 sequentially.

Preferably, the step of activating transducer or each sensor 21 of the plurality comprises activating each transducer or sensor 21 of a predefined subset of transducers or sensors 21. The subset can be programmed in advance into the control unit 300. The subset can also be defined in real-time meaning that the control unit 300 is learning and deciding itself how the patterns are changing or should be changed.

After performing the comparison, the comparison result is sent to the control unit 300.

This process is repeated for each transducer or sensor 21 of the plurality (array).

The cell activity or "spike" is illustrated in FIG. 7, where the voltage versus the time required to scan is shown (scanning performed by detection unit). In an example such a "spike" has a typical duration of 1 ms. This time is given by $t_s \times (M \times N)$ being the time spent on one transducer or sensor 21, whereby $t_s$ is the scanning time and (M×N) represents the number of sensors to be scanned. This number can be the total number of sensors of an array or can represent the number of sensors to be scanned according to a predefined subset. Such pattern can be defined and memorized in the control unit before the detection and recording process or can be defined in real-time during the scanning process and adapted according to the detection results.

The scanning of the transducer or sensor array 21 or of a subset of transducer or sensor 21 of the array lasts for a period inferior to a half of the time of a "spike", to ensure that no activity is missed and that the peak of the "spike" can be recorded.

Figure 10:
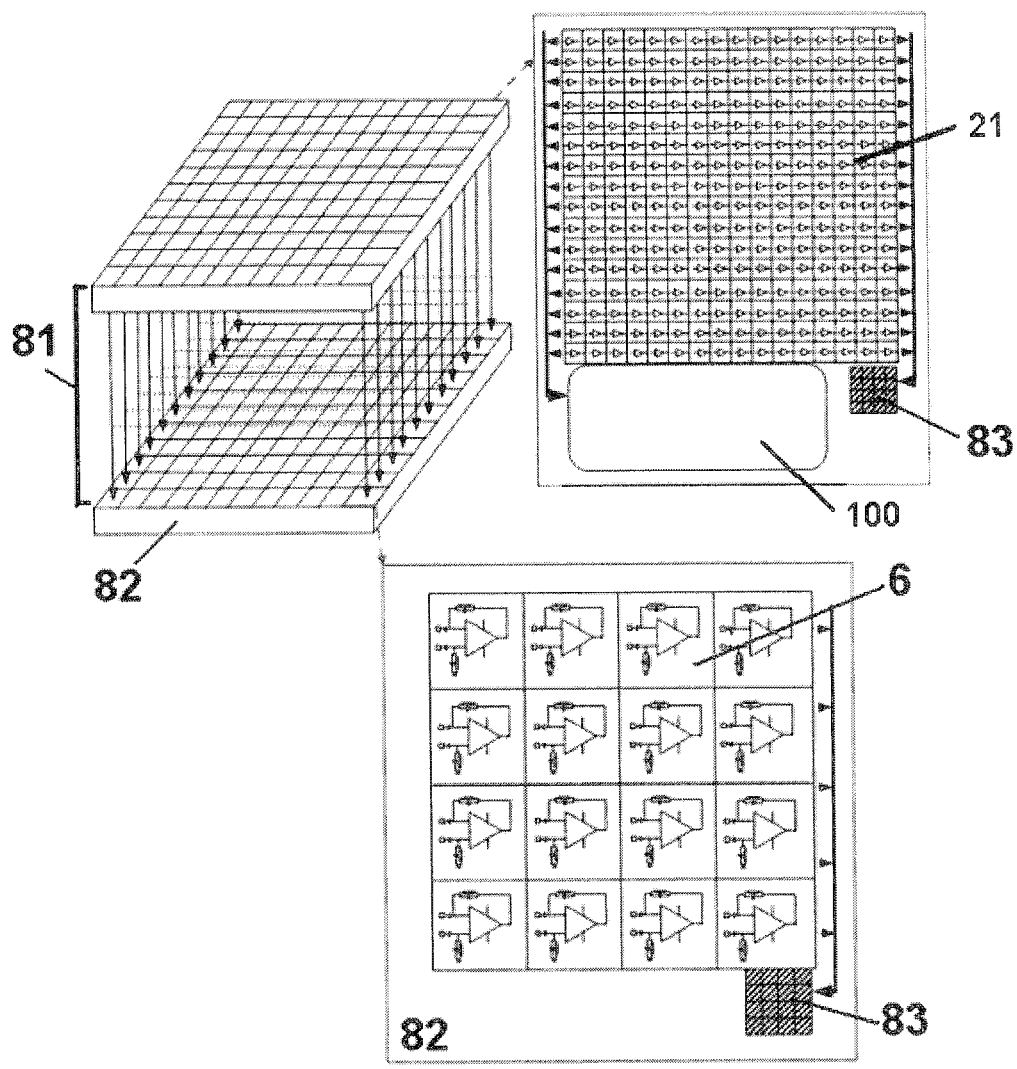
FIG. 10 represents an example using 3D integration technology accordingly to the present disclosure.

According to another embodiment, the transducer or sensor array 21 is arranged in a 3D integrated system as illustrated in FIG. 10.

A plurality of transducer or sensors arrays 21 can be implemented on several top dies 81.

The bottom die 82 has a number of recording channels. The number of recording channels is preferably based on the available area in the bottom die.

The transducers or sensors 21 on the top die can be routed to any of the recording channels on the bottom die through the 3D vias 83.

This way, given that the area is fixed, a larger number of recording channels are available for each layer or sub-array than would be if only a single die would be used.

In a preferred embodiment, two dies are connected to each other using 3D through via Arrays. The top die has an X×Y array comprised of M×N subarrays of transducers. The bottom die has N recording channels. The number of channels is based on the available area in the bottom die. The transducers or sensors 21 on the top die can be routed to any of the N channels on the bottom die through the 3D vias. This way, given that the area is fixed, a larger number of channels are available for each subarray than would be if only a single die would be used. The recording channels can also be used for stimulation, by placing stimulation circuitry (stimulation unit) on the bottom die. Both dies can be made in separate technologies to optimize the readout and reduce costs.

According to a preferred embodiment of the present disclosure, the transducer or sensor 21 array has been implemented in the form of a 16×16 array in AMIS 0.35 μm technology. The array has a detection unit comprising buffers inside the transducer or sensor 21, sample and hold capacitors, crude amplification system and comparators as mentioned above. If a cell activity occurs crude amplifiers in conjunction with the buffers and the sample and hold will amplify this signal and the comparators will generate a logical signal. This will be detected by the control unit 300 which will route an available recording channel to the respective transducer or sensor 21. The recording channel is a first stage low noise and low power, fine amplifier. The control unit 300 is represented by an external FPGA which sends control signals to the chip. A neural spike lasts for about 1 ms. The detection unit scans through the array with in 410 μs. The recording channels are reset with in 40 μs. Therefore the in the worst case scenario, 450 μs out of 1 ms of the spike will be missed. This is with in the target of less than half in order to be able to record the peak.

In one embodiment of the present disclosure, the transducer or sensor 21 array are arranged to form a matrix comprising X columns and Y rows.

Preferably, the transducer or sensor 21 array is divided into S transducer or sensors 21 subarrays.

Preferably, each subarray i (i=1, . . . S) comprises $M_i$ columns and $N_i$ rows.

More preferably, the sum of $M_i$ (i=1, . . . S) is equal to X.

More preferably, the sum of $N_i$ (i=1, . . . S) is equal to Y.

Preferably, each subarray i comprises a detection unit.

Preferably, each subarray i comprises a recording unit.

Preferably, the transducer or sensor 21 array comprises at least one control unit.

Preferably, each subarray i comprises a control unit.

Preferably, the transducer or sensor 21 array further comprises post-processing means.

Preferably, the transducer or sensor 21 array further comprises at least one stimulation unit for sending stimulation signals to the transducer or sensor.

According to preferred embodiments, the device of the present disclosure comprises a sensor array having a plurality of sensors arranged for stimulating neurons and recording neural activity.

The array comprises a first and a second amplifying block and a digital control block as presented in FIG. 2. The first amplifying block is arranged for detecting neural activity in the form of a spike. The control unit is responsible for the addressing of the sensors for the neural activity detection system and to generate the necessary control signals as well as the routing information for the recording channels. The second amplifying block is arranged for recording the neural activity. Recording channels are designed for low noise recording of this neural activity. The basic concept is to allocate recording channels based on neural activity rather than permanently routing them or multiplexing and recording all the sensors and generating unnecessary data.

The first amplifying block or Neural Activity Detection system comprises buffers present in the sensors, sample and hold capacitors, crude amplifiers, and comparators as shown in FIG. 2. The neural Activity Detection system quickly scans through the subarray to detect any spike occurring at any of the sensors in the array. The scanning is done in less than half the time of a spike, to ensure that no activity is missed and that the peak of the spike can be recorded. FIG. 7 shows a spike, with the time required to scan shown. This time is given by $t_s \times (M \times N)$, $M \times N$ being the size of the array and $t_s$ being the time spent on one sensor.

The second amplifying block or Neural Recording System comprises low noise, low power, fine amplifiers. This system may also comprise a post-processing system. The control unit may comprise an on-chip controller or an FPGA or any other microcontroller known to the person skilled in the art.

An example system has been implemented in the form of a 16×16 array in AMIS 0.35 μm technology. The array has a neural activity system comprising buffers inside the sensors, sample and hold capacitors, a crude amplification system and the comparators as mentioned above. If a neural activity occurs crude amplifiers in conjunction with the buffers and the sample and hold will amplify this signal and the comparators will generate a logical one. This will be detected by the control unit which route an available recording channel to the respective sensor. The recording channel is a first stage low noise and low power fine amplifier. The control unit is represented by an external FPGA which sends control signals to the chip. A neural activity detection system scans through the array with in 410 μs. The recording channels are reset with in 40 μs; $t_s$ and $t_r$, are shown respectively in FIG. 7. Therefore, in the worst case scenario, 450 μs out of 1 ms of the spike will be missed. This is within the target of less than half in order to be able to record the peak.

The buffers present in each sensor are implemented as gated source followers. The schematic of a sensor is shown in FIG. 4. A sensor is only activated, by the Activate N switch as shown in FIG. 9, when it is addressed. This helps to conserve power. The sample and hold capacitors are shown in FIG. 6. There are two pairs of sample and hold capacitors. Each pair has a signal capacitor and a reset capacitor which is needed to remove the offset in the source followers. The signal capacitors samples and holds the signal plus the offset present in the source follower while the reference capacitor holds just the offset by resetting the source follower by activating the reset switch as shown in FIG. 4. This helps to remove the offset. Having two pair of sample and hold capacitors helps to reduce power. One pair of capacitors samples the signal from the currently addressed sensor while the other pair holds the value of the previously addressed sensor for the crude amplifiers. The same complete time (1.6 μs) is used to address a sensor, to sample the signal and the same complete time (1.6 μs) is required to amplify the signal by the crude amplifiers. This reduces the bandwidth requirement to the source follower as well as the crude amplifiers as well as the comparators. This in turn helps to conserve power at the cost of some area from the two extra capacitors.

The crude amplifiers are designed for high bandwidth, high gain, and area and compromised on noise and gain error since the primary function of these is not to record the activity but just to detect it. High gain is required to overcome the mismatch in the comparators. The highest gain needed is defined by the estimated mismatch in the comparator divided by the smallest signal that has to be detected. The detection threshold for the comparators can be set externally to an acceptable level above the noise. The offset in the amplifiers is removed by output offset cancellation. The crude amplifiers connected to the sample and hold capacitors are shown in FIG. 5. The amplification can be selected as 57.8 dB or 77.1 dB by setting a switch.

The recording channel is represented by a first stage low noise, low power, fine amplifier as shown in FIG. 8. The gain of this amplifier is 24 dB.

Figure 9A:
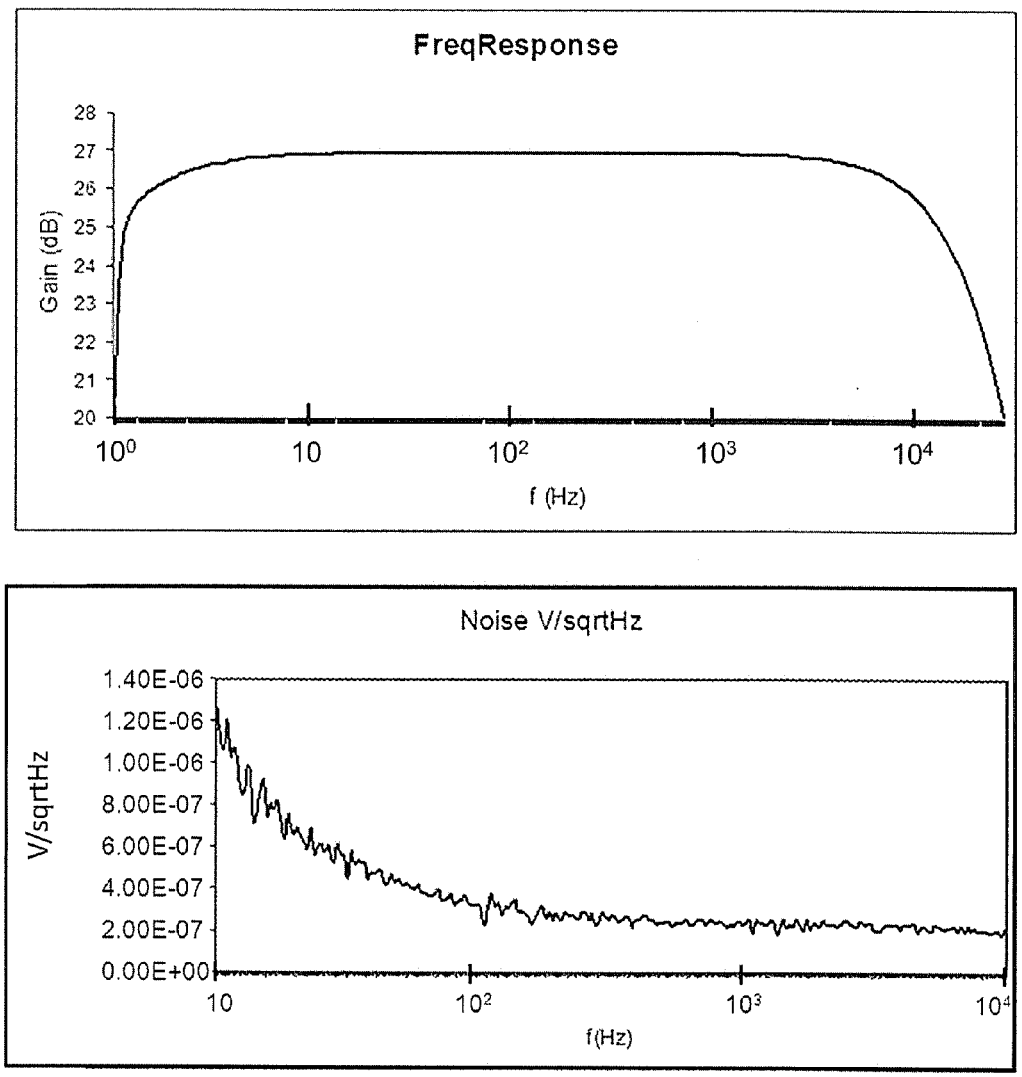
FIG. 9($a$) represents an example of frequency response and noise measurements of a fine amplifier comprised in the recording unit according to the present disclosure.
Figure 9B:
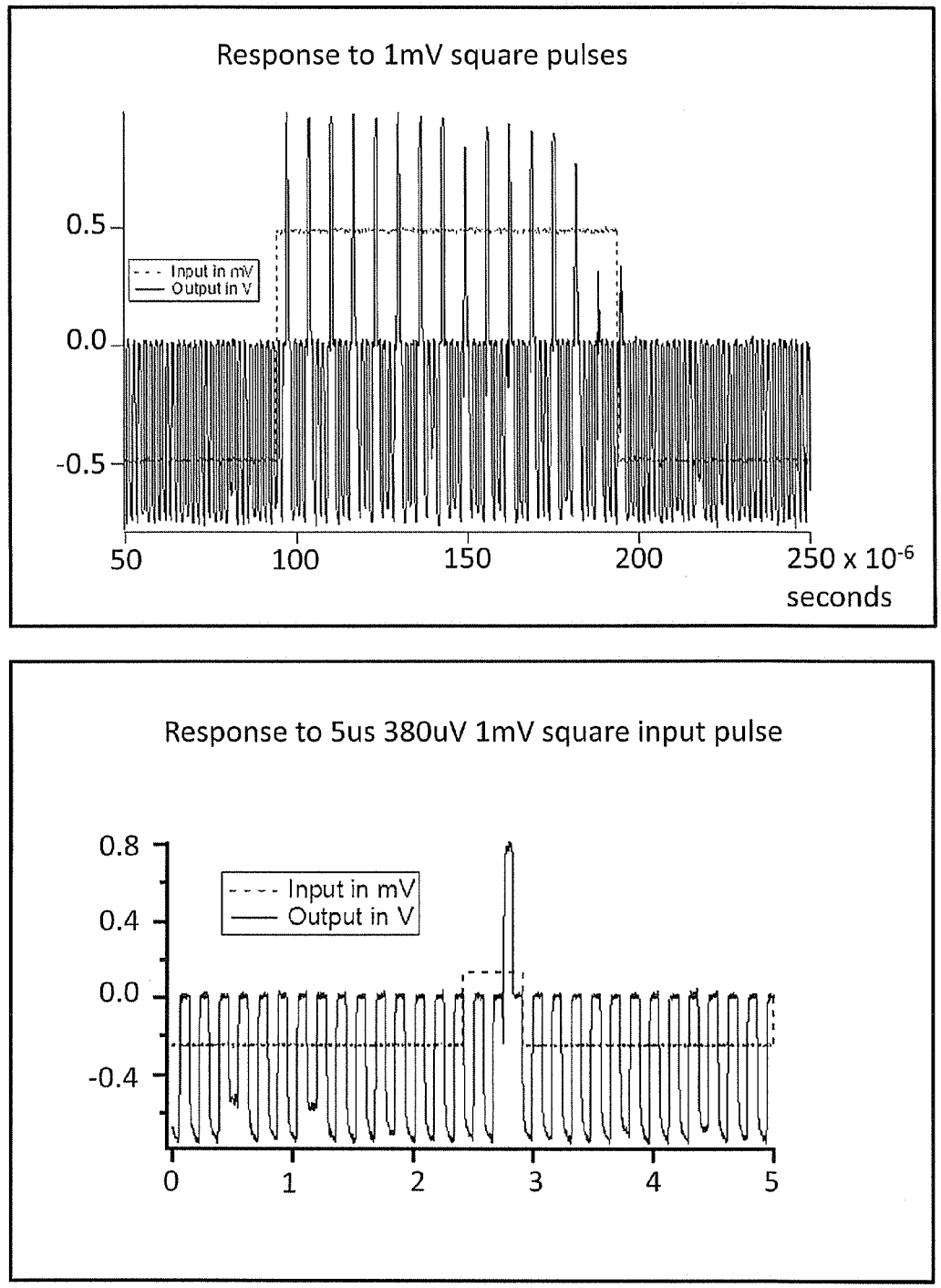

The power consumption is 9 μW. Integrated noise between 100 Hz-5 kHz is 11.628 μVrms. The frequency response of the fine amplifier as well as noise measurements are shown in FIG. 9(a). Measurements of the Neural Activity Detection system are shown in FIG. 9(b). It shows the output of the crude amplifiers after a square wave is given as an input to one of the sensors through a capacitively coupled input. The scanning is being done between four sensors.

The control unit is implemented in the form of a programmed FPGA.

Using the 3D integration capabilities the concept can be further expanded as shown in FIG. 10. Two dies are connected to each other using 3D through via Arrays. The top die has a X×Y Array comprised of M×N sub-arrays of sensors as mentioned above. The bottom die has N recording channels. The number of channels is based on the available area in the bottom die. The sensors on the top die can be routed to any of the N channels on the bottom die through the 3D vias. This way, given that the area is fixed, a larger number of channels are available for each sub-array than would be if only a single die would be used.

These same channels can also be used for stimulation, if stimulation circuitry is placed on the bottom die. Both dies can be made in separate technologies to optimize the readout and reduce costs.

The invention claimed is:

1. An active interface device comprising:
   a transducer or sensor array comprising a plurality of transducers or sensors arranged to transform a cell activity into an electrical signal, each transducer or sensor comprising a switch for activating the transducer or sensor;
   at least one detection unit configured to detect one or more electrical signals generated by the transducer or sensor array, wherein the detection unit comprises at least one comparator configured to compare the one or more electrical signals to a predetermined threshold signal;
   at least one recording unit configured to record the one or more electrical signals and having a plurality of recording channels to electrically connect to the transducers or sensors in real-time, wherein the recording channels are resources at a disposal of the transducer or sensor array to record cell activity;

a first die and a second die coupled to the first die, wherein the plurality of transducers or sensors is arranged on the first die, wherein the plurality of recording channels is arranged on the second die;
a three-dimensional via array that provides a plurality of electrical connections through the first die to the second die, wherein the plurality of transducers or sensors are operable to be switchably electrically connected to the plurality of recording channels using at least one electrical connection provided by the three-dimensional via array;
at least two amplifying blocks for amplifying the one or more electrical signals, wherein a first amplification is performed by a first amplifying means disposed in the detection unit and a second amplification is performed by a second amplifying means disposed in the recording unit, wherein an amplitude of the predetermined threshold signal is greater than a noise level of the first amplifying means; and
at least one control unit configured to:
  determine a cell activity based on the comparison between the one or more electrical signals from the first amplifying means and the predetermined threshold signal; and
  responsive to determining the cell activity, activate the second amplifying means associated with respective transducers or sensors corresponding to the determined cell activity by turning on the switch of the respective transducer or sensor; and
  further responsive to determining the cell activity, route an electrical signal from a respective activated transducer or sensor to an available recording channel using at least one electrical connection provided by the three-dimensional via array.

2. The device according to claim 1, wherein a ratio of the gain between the first amplifying means and the second amplifying means is at least 5.

3. The device according to claim 2, wherein the ratio of the gain between the first amplifying means and the second amplifying means is at least 10.

4. The device according to claim 1, wherein the first amplifying means is faster than the second amplifying means.

5. The device according to claim 1, wherein the first amplifying means generates more noise than the second amplifying means.

6. The device according to claim 1, wherein the control unit is configured to scan each transducer or sensor in the array in a time equal to less than one half of an expected width of a detected electrical signal spike at each of the transducers or sensors in the array.

7. The device according to claim 1, wherein each recording channel comprises at least one stage of amplification.

8. The device according to claim 1, wherein the plurality of transducers or sensors corresponds to a first given number of transducers or sensors, wherein the plurality of recording channels to electrically connect to the transducers or sensors in real-time corresponds to a second given number of recording channels, wherein the second given number is less than the first given number, and wherein the device is configured such that each transducer or sensor can be connected to at least one recording channel through at least one electrical connection provided by the three-dimensional via array.

9. The device according to claim 8, wherein each recording channel is not permanently connected to a given sensor or transducer, such that each recording channel can be routed, based on real-time needs for recording detected cell activity, to different sensors or transducers of the plurality of sensors or transducers.

10. The device according to claim 1, wherein the cell activity comprises at least one of a mechanical stress, a release of ions, a release of neurotransmitters, or an electrical signal.

11. A biosensing system comprising the active interface device of claim 1.

12. A method for recording cell activity from a transducer or sensor array comprising a plurality of transducers or sensors, the method comprising:
  a) addressing one or more transducers or sensors of the array;
  b) activating the transducer or sensor by activating a switch coupled to the transducer or sensor;
  c) receiving from the activated transducer or sensor an electrical signal indicative of cell activity;
  d) amplifying the electrical signal, wherein the amplifying comprises at least two amplifications comprising (i) a first amplification performed via a first amplifying means having a high gain followed by (ii) a second amplification performed via a second amplifying means having a low gain;
  e) comparing the electrical signal from the first amplifying means to a predetermined electrical threshold signal to generate a comparison result, wherein an amplitude of the predetermined threshold signal is greater than a noise level of the first amplifying means;
  f) determining, using the comparison result, that the electrical signal corresponds to cell activity;
  g) in response to determining that the electrical signal corresponds to cell activity, electrically connecting in real-time, via the second amplifying means, an available recording channel to the activated transducer or sensor corresponding to the determined cell activity, wherein the plurality of transducers or sensors is arranged on a first die, wherein the plurality of recording channels is arranged on a second die coupled to the first die, wherein a three-dimensional via array provides a plurality of electrical connections through the first die to the second die, wherein the plurality of transducers or sensors are configured to be switchably electrically connected to the plurality of recording channels using at least one electrical connection provided by the three-dimensional via array; and
  h) recording the electrical signal from the activated transducer or sensor.

13. The method according to claim 12, wherein the first amplification is performed during a detection stage defined by steps a) to f), and the second amplification is performed during a recording stage defined by steps g) to h).

14. The method according to claim 12, wherein a sequence of steps a) to h) for a next or subsequent transducer or sensor in the array starts between steps c) and d) of a present transducer or sensor in the array.

15. The method according to claim 12, wherein the steps a) to h) are repeated for a next or subsequent transducer or sensor.

16. The method according to claim 12, further comprising, after step h), a step of sequentially sending the recorded electrical signal(s) to a post-processing unit.

17. The method according to claim 12, wherein the step of determining in step f) is performed by a control unit.

18. The method according to claim 12, wherein a ratio of the gain between the first amplifying means and the second amplifying means is at least 5.

19. The method according to claim 18, wherein a ratio of the gain between the first amplifying means and the second amplifying means is at least 10.

20. The method according to claim 12, wherein a time to scan each transducer or sensor in the array is less than one half of an expected width of a detected electrical signal spike at each of the transducers or sensors in the array.

21. The method according to claim 12, wherein the cell activity comprises at least one of a mechanical stress, a release of ions, a release of neurotransmitters, or an electrical signal.

\* \* \* \* \*